United States Patent [19]
Freytag et al.

[11] Patent Number: 4,517,303
[45] Date of Patent: May 14, 1985

[54] SPECIFIC BINDING ASSAYS UTILIZING ANALYTE-CYTOLYSIN CONJUGATES

[75] Inventors: J. William Freytag, Wilmington; William J. Litchfield, Newark, both of Del.

[73] Assignee: E. I. Du Pont de Nemours and Company, Wilmington, Del.

[21] Appl. No.: 435,455

[22] Filed: Oct. 20, 1982

[51] Int. Cl.³ .................... G01N 33/54; G01N 33/50; G01N 33/74
[52] U.S. Cl. ........................... 436/501; 435/4; 435/5; 435/7; 435/21; 435/36; 436/512; 436/520; 436/541; 436/803; 436/813; 436/815; 436/817; 436/827; 436/828; 436/829
[58] Field of Search ............... 436/512, 532, 533, 534, 436/808, 828, 829, 501, 520, 541, 803, 813, 815, 817, 827; 435/4, 5, 7, 21, 36

[56] References Cited

U.S. PATENT DOCUMENTS 4,235,792 11/1980 Hsia et al. ........................ 260/403
4,342,826 8/1982 Cole ................................. 435/7
4,372,745 2/1983 Mandle ........................... 436/537

FOREIGN PATENT DOCUMENTS 2069133 8/1981 United Kingdom .................... 33/54

OTHER PUBLICATIONS

Chemical Abstracts, 94:43718y (1981).
K. Uemura et al., Jour. of Immunological Methods, 53, 221-232 (1982).
Haga et al., Liposome Immunosensor for Theophylline, Biochem., Biophys. Res. Commun., vol. 95, 187-192 (1980).
Haga et al., Drug Sensor: Liposome Immunosensor for Theophylline, Anal. Biochem., vol. 118, 286-293 (1981).
Hsia and Tan, Membrane Immunoassay, New York Acad. Sci., vol. 308, 139-148 (1978).
Thelestam and Mollby, Plant and Animal Cytolysins, Biochem. Biophys. Acta, vol. 557, 156-169 (1979).
Sessa et al., Interaction of a Lytic Polypeptide, Melitin, with Lipid Membrane Systems, J. Biol. Chem., vol. 244, 3575 (1969).

Primary Examiner—Sidney Marantz

[57] ABSTRACT

A novel analyte-cytolysin conjugate and its use in a lipid vesicle mediated measurement process is described for a wide variety of analytes present at very low concentration. The method involves forming a reaction system consisting of analyte, analyte specific binding agent, analyte-cytolysin conjugate, and vesicles containing detectable marker material in such proportions that uncombined conjugate alters the permeability of the vesicles resulting in the release and quantitative detection of marker material which can be correlated with the amount of analyte initially present.

40 Claims, 2 Drawing Figures

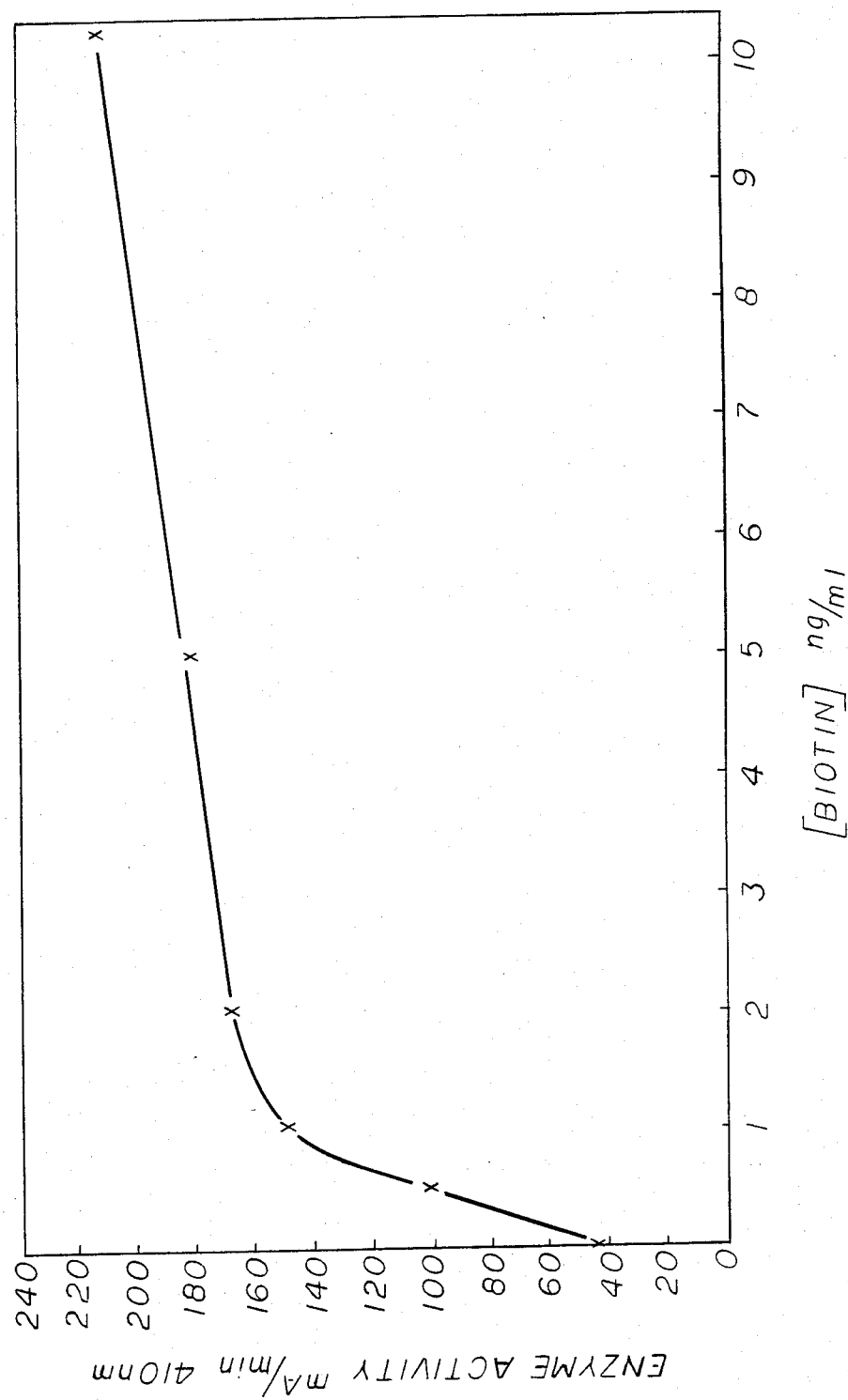

SPECIFIC BINDING ASSAYS UTILIZING ANALYTE-CYTOLYSIN CONJUGATES

TECHNICAL FIELD

This invention relates to a highly sensitive and rapid method of analysis for the quantitative determination of the amount of a specific analyte in liquid medium, and to novel analyte-cytolysin conjugates which alter the membrane permeability of vesicles containing marker material.

BACKGROUND OF THE INVENTION

Clinical laboratory chemical diagnostic tests are an important component of health care delivery. The utilization of these tests by physicians to monitor drug levels where only a narrow therapeutic range exists, to guide decisions on treatment and surgical options, and to screen patients for the early detection of disease has rapidly increased the number of tests performed annually. With almost 6 billion tests performed in 1976 and 12.2 billion estimated to be performed in 1986 [Luning Prak Associates Survey, 1980], speed, accuracy, and cost control are important objectives. The desire to measure such analytes as drugs, hormones, and metabolites at micromolar ($\mu$M) to picomolar (pM) levels in complex body fluid matrices has led to the development of sophisticated test methodology which can be implemented by automated techniques at reasonable cost.

Broadly applicable, accurate screening assays are therefore needed to monitor the presence and quantity of biological materials. Various methods have been utilized in the past including liquid and gas chromatography, mass spectrometry, and numerous bioassay techniques. These methods are time consuming and not easily applied in large-scale, automated screening programs.

In recent years, a number of immunoassay techniques have been developed to take advantage of the specificity of antibody reactions while avoiding the complicating features of radiochemical labelling. The use of vesicles containing sequestered detectable marker material can provide a stable, sensitive, and flexible measurement system for quantifying such medically important materials as cardiac glycosides, antibiotics, therapeutic drugs, hormones, and vitamins. In addition, methods of analysis for toxins, food and packaging additives, and environmental pollutants at extremely low concentration are required.

Haga et al. [Biochem. Biophys. Res. Commun., Vol. 95, 187–192 (1980) and Anal. Biochem., Vol. 118, 286–293 (1981)] describe a liposome-based immunoassay in which horseradish peroxidase is sequestered within a lipid vesicle formed from a mixture of lecithins including phosphatidylethanolamine to which analyte has been covalently bonded. The lipid vesicle is therefore specific for the analyte of interest, and lysis is induced by complement (from guinea pig serum) in combination with the antibody specific for the analyte. Such systems require the preparation of lipid vesicles with specific analyte "tags" and also the use of the unstable, complex complement system to release the detectable marker material used to quantify the amount of analyte initially present. Long incubation periods are frequently required which increase analysis time.

Hsia et al. [New York Academy Sci., Vol. 308, 139–148 (1978) and U.S. Pat. No. 4,235,792] describe complement mediated immunoassay techniques wherein the lysis of lipid vesicle with a synthetic sensitizer incorporated in the lipid bilayer leads to the release of marker material, in particular of spin labelled molecules quantified by electron spin resonance techniques. The assay system requires the preparation of a specific lipid vesicle for each analyte of interest to mediate attack and lysis by the complement system in the presence of antibody.

U.K. Patent Application No. 2069133A and U.S. Pat. No. 4,342,826 describes a process for sequestering enzyme marker within lipid vesicles in a manner which enhances the so-called signal to noise ratio of the reagents. The lipid vesicles must be specifically labelled with either antigen or antibody to render them immunoreactive in the presence of complement.

Thelestam et al. [Biochem. Biophys. Acta, Vol. 557, 156–169 (1979)] describe a variety of microbial, plant, and animal cytolysins and efforts to classify cytolysins by measuring changes in the permeability of human fibroblasts. Melittin, the polypeptide lytic factor of bee venom, was among those agents tested, but no immunodiagnostic or analytical applications of the cytolytic agents are disclosed, and the effect on synthetic lipid vesicles was not considered.

Sessa et al. [J. Biol. Chem., Vol. 244, 3575–3582 (1969)] examine the mechanism by which melittin disrupts or lyses biomembranes using both erythrocytes and lipid vesicles as model systems. No disclosure of melittin-analyte conjugates or their relevance to immunodiagnostic analytic methods is made.

At this time there exists a clear need for membrane lytic immunoassay systems which do not require unstable complement or specific antigen or antibody tagged vesicles. A system in which specificity resides in a lytic agent would provide great flexibility since the same sequestered marker vesicle preparation would be utilized in all assays. Such a system could also incorporate a variety of detectable marker materials to take advantage of the instrumental methods available to the user.

Summary of the Invention

A sensitive, homogeneous assay to measure analytes in solution has been discovered which utilizes novel analyte-cytolysin conjugates and vesicles containing marker material wherein the vesicle membrane permeability changes resulting from interaction with such conjugates can be modulated by analyte-specific binding agent. The assay also utilizes a standard vesicle preparation applicable for analysis of a wide variety of analytes by many different instrumental methods. Specifically, one aspect of this invention involves the synthesis of an analyte-cytolysin conjugate wherein at least one analyte derivative molecule is attached per cytolysin molecule such that said conjugate is capable of both reacting with binding agent of the analyte and altering vesicle membrane permeability to release marker material. Another aspect of this invention is a method for determining the amount of an analyte in liquid medium comprising the steps of:

(A) forming a reaction system by contacting said liquid medium with
  (1) analyte specific binding agent;
  (2) analyte-cytolysin conjugate; and
  (3) vesicles containing marker material sequestered within the vesicle in proportions such that the interaction of unbound analyte-cytolysin conjugate with said vesicles results in the release of said marker material; and (B) measuring said marker material thereby released which is related to the amount of said analyte initially present in said liquid medium.

An antibody molecule is capable of functioning as an analyte in the present invention, but an antibody-cytolysin conjugate can have utility in a heterogeneous assay wherein a separation of reaction products occurs prior to the measurement step. Another aspect of this invention therefor involves a novel antibody-cytolysin conjugate.

BRIEF DESCRIPTION OF THE DRAWINGS

FIG. 2 is a standard assay curve to be used for analysis of biotin which relates the amount of marker material released from lipid vesicles by unbound biotin-melittin conjugate to the concentration of biotin initially present in the liquid medium.

DETAILED DESCRIPTION OF THE INVENTION

Figure 1:
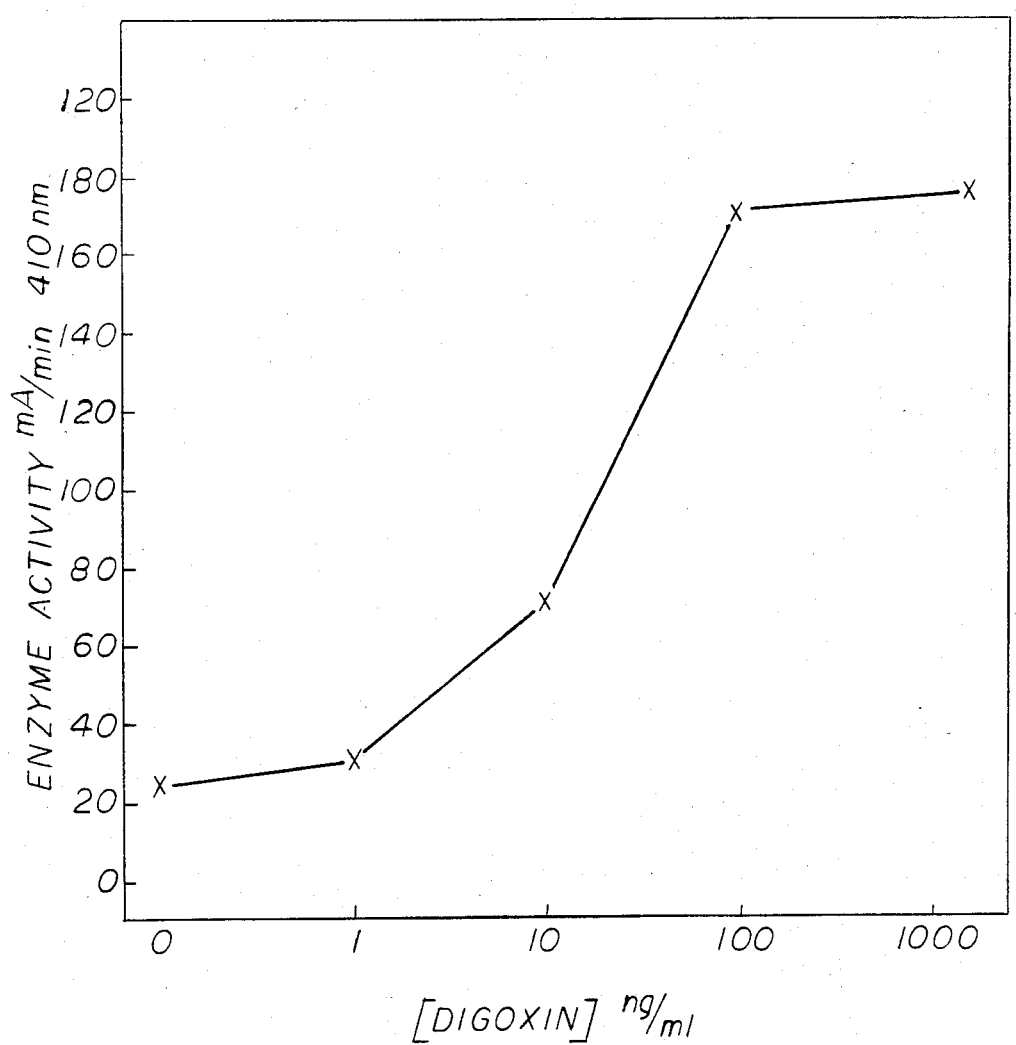
FIG. 1 is a standard assay curve to be used for digoxin analysis which relates the amount of marker material released from lipid vesicles by unbound ouabain-melittin conjugate to the concentration of digoxin initially present in the liquid medium.

This invention provides a sensitive method and novel materials for detecting and/or determining the amount of a wide variety of organic materials present in clinical, environmental, and other test samples. In the context of this disclosure, the following terms shall be defined as follows: "analyte" is the substance, or group of substances, whose presence or amount in a liquid medium is to be determined, which additionally have the capability of being attached to a cytolysin substance to form a analyte-cytolysin conjugate; "cytolysin" is any substance or agent of molecular weight from about 100–100,000 daltons which can change the permeability of biomembranes; "analyte derivative" refers to both unmodified and chemically modified analyte molecules, and/or their chemical combinations with spacer arms, which can be chemically bound to cytolysin molecules by covalent, ionic, or other bonding techniques; "spacer arm" is a bifunctional molecule used to chemically bond an analyte derivative to a cytolysin molecule while maintaining some distance between the two molecular entities; "binding agent" is any substance, or group of substances, which has specific binding affinity for the analyte to the exclusion of other substances such that reaction occurs between a particular analyte and binding agent to form a bound complex; and "binding analog of the analyte" is any substance, or group of substances, which behaves essentially the same as the analyte with respect to binding specificity for the binding agent for the analyte; "vesicles" are either natural or synthetic sacs believed to consist of lipid bilayers which separate an internal compartment which can sequester marker material from the external media in which the vesicles are suspended; and "marker material" is any substance sequestered within a vesicle which is not detectable by instrumental methods until released from the vesicle, or until rendered detectable by another substance which as a result of an alteration in vesicle membrane permeability followed by diffusion into the vesicle and be chemical modified to a substance which is detectable by instrumental methods.

The present homogeneous method may be applied to the detection of any analyte for which a binding agent exists. The binding agent may consist of an antibody in the form of whole antiserum, an IgG fraction, as affinity-purified monospecific material, a monoclonal antibody, a monovalent antibody or of other specific binding proteins like lectins, hormone receptors, or serum transport proteins. The quantitative measurement aspect of the invention results from the fact that free analyte present in the test sample and the analyte-cytolysin conjugate are both capable of reacting in a competitive fashion with binding agent. In the absence of analyte, the concentration of the process components is adjusted such that there is no release of sequestered marker material from the vesicles. In the presence of analyte, excess analyte-cytolysin conjugate exists which alters the permeability of the vesicles resulting in a release of marker material at a rate and in an amount proportional to the amount of analyte initially present. An amplification is obtained in the measurement process due to the fact that a single interaction between an analyte-cytolysin conjugate and a vesicle can result in the release of a large number of detectable marker material molecules.

Various protocols can be employed in assaying for a wide variety of analytes. The determination of the amount of analyte initially present in the test sample can be carried out by correlation with either the amount of marker material released after a given contact time of reagents, or with the rate of release of such marker material under conditions which enable comparison with a standard curve produced for known amounts of the reagents. Contacting times of the reagents can vary from 10 seconds to one hour at temperatures in the range of from about 4° to 40° C. and at a pH in the range of about 5–10, usually 6–8. The measurement can be carried out manually, or with reagents packaged to utilize automated analyzers.

To illustrate the analyte-cytolysin conjugate and homogeneous assay of the instant invention, an aliquot containing an unknown amount of analyte is added to buffered incubation medium containing substrate for the enzyme which is used as marker material sequestered in the vesicles. A known amount of antibody specific for the analyte is added to the medium and briefly incubated prior to the addition of a known amount of analyte-cytolysin conjugate. After further brief incubation, a known amount of vesicle preparation is added and the amount of substrate converted by enzyme after diffusion into the vesicle is monitored as a function of time. Comparison with a standard curve relating analyte concentration with substrate conversion obtained under the same conditions of time intervals and reagent amounts enables the determination of the unknown amount of analyte.

The antibody-cytolysin conjugate of the present invention can be used in a heterogeneous assay for the detection of any analyte which has antigenic or haptenic properties, i.e., the ability to elicit the formation of anti-analyte antibody when injected into a host. To illustrate the use of an antibody-cytolysin conjugate in a heterogeneous assay, an aliquot containing an unknown amount of analyte is mixed with a buffered solution containing cytolysin labeled anti-analyte antibody (C-Ab). The C-Ab should be in molar excess over the highest concentration of analyte expected to be found in a clinical sample. The mixture is then incubated during which time a fraction of the C-Ab will immunochemically bind to analyte while the other fraction of C-Ab will remain free. After incubation, the bound and free C-Ab are separated from one another. In one embodiment, the separation can be carried out using an affinity column which contains a packing material to which analyte is immobilized, either directly or through a spacer arm. The mixture is applied to the affinity column. As the sample percolates through the column, the free C-Ab will bind to the immobilized analyte. Consequently, only the Analyte-(C-Ab) complex will elute from the column. If analyte is substantially larger than C-Ab, the mixture can be applied to a size exclusion column such as Sepharose 4BCl, a crosslinked macroporous agarose in bead-form for gel permeation chromatography from Pharmacia Fine Chemicals. The void volume containing the complex is collected. The eluate or void volume depending on which separation step is employed is then mixed with suspension of vesicles. The cytolysin moiety of the complex will effect a change in permeability of the vesicle membrane allowing marker material to be released in the external medium. The marker material will be either directly detectable (e.g., chromophores) or indirectly detectable (e.g., an enzyme which will combine with a specific substrate in the external medium to yield a detectable product).

Analyte

This invention can be applied to the detection and measurement of a broad variety of analytes to which binding agents are available such as drugs of biological and clinical importance, metabolites, vitamins, pesticides, steroids, peptide hormones and certain cancer markers.

Analytes of particular interest include those drugs and hormones with either very low concentrations in biological fluids or with narrow therapeutic ranges. The cardiac steroid digoxin satisfies both criteria since levels below 0.8 ng/ml (nanograms per milliliter) in human serum are ineffective for treating cardiac arrhythmia while levels above 2.0 ng/ml are often toxic. Other analytes similarly present at low concentration or with narrow therapeutic range include vitamin $B_{12}$, folate, and most of the steroid, peptide, and protein hormones. Analytes such as myoglobin normally have very low levels in serum that can rise dramatically after myocardial infarction and are therefore indicative of this condition. Analytes such as microbial and cancer cell markers would generally be low in concentration since early detection (prior to prolonged cell growth) is highly desirable. Aminoglycoside drugs, barbiturate drugs, and many of the miscellaneous drugs such as theophylline are relatively high in concentration with μg/ml (microgram/milliliter) levels but have narrow therapeutic ranges. Table I lists a variety of analytes of particular interest in practicing the instant invention.

The existence of binding analogs of the analyte, for example ouabain for digoxin, can be extremely advantageous by enabling reagents developed for one assay to be used in another for a group of related substances, and by providing choices of binding properties to those skilled in the art which simplify the isolation and purification of binding agents.

TABLE I
| ANALYTES |
| --- |
| Alkaloid Drugs |
| benzoyl ecgonine |
| cocaine |

TABLE I-continued
| ANALYTES |
| --- |
| codeine |
| dextromethorphan |
| heroin |
| lysergic acid |
| morphine |
| quinidine |
| quinine |
| Aminoglycoside Drugs |
| amikacin |
| gentamicin |
| kanamicin |
| neomicin |
| tobramicin |
| Antibiotic Drugs |
| actinomycetin |
| caromycin |
| chloramphenicol |
| chloromycetin |
| chlortetracycline |
| erythromycin |
| oxytetracycline |
| penicillin |
| polymyxin B |
| terramycin |
| tetracycline |
| streptomycin |
| Barbiturate Drugs |
| diphenylhydantoin |
| ethosuximide |
| phenobarbital |
| primidone |
| secobarbital |
| Marijuana Derivatives |
| cannabinol |
| tetrahydrocannabinol |
| Metabolites |
| galactose |
| phenylpyruvic acid |
| porphyrin |
| spermine |
| Miscellaneous Drugs |
| amitriptyline |
| anticholinergic drugs |
| antihistamines |
| atropine |
| butyrophenones |
| caffeine |
| carbamazepine |
| chloropromazine |
| epinephrine |
| griseofulvin |
| imipramine |
| L-dopa |
| lidocaine |
| meperidine |
| meprobamate |
| methadone |
| N—acetyl procainamide |
| narceine |
| nortriptyline |
| oxazepam |
| papaverine |
| procainamide |
| propanolol |
| prostaglandins |
| tegretol |
| theophylline |
| serotonin |
| valproic acid |
| Peptide Hormones |
| adrenocorticotropin (ACTH) |
| angiotensin |
| met- and leu-enkephalin |
| oxytocin |
| thyroxine |
| triiodothyronine |
| vasopressin |
| Pesticides |
| carbamate pesticides |

TABLE I-continued
ANALYTES thiophosphate pesticides
polyhalogenated biphenyl pesticides
polyhalogenated sulfonamide pesticides Steroids adrenocorticol steroids
androgens
bile acids
digoxin
digoxigenin
diethylstilbestrol
estrogen
gestrogen Toxins in Food aflatoxins
ipomeamerone
mycotoxins
ochratoxin
patalin
penicillic acid
tricothecene toxin
zearclonone Vitamins biotin
folic acid
thiamine
vitamin A
vitamin $B_2$
vitamin $B_6$
vitamin $B_{12}$
vitamin C
vitamin D
vitamin E
vitamin K Protein Hormones chorionic gonadotropin
chorionic thyrotropin
glucagon
insulin
nerve growth factor
parathyroid hormone
placental lactogens
prolactin
proinsulin
relaxin Proteins albumin
$\alpha_1$-acid glycoprotein
$\alpha_1$-antitrypsin
$\alpha_1$-glycoprotein
$\alpha_1$-lipoprotein
$\alpha_2$-antitrypsin
$\alpha_2$-macroglobulin
$\alpha_2$-glycoprotein
$\alpha_2$-lipoprotein
$\beta$-lipoprotein
$\beta$-glycoprotein
c-reactive protein
fibrin split products
fibrinogen
immunoglobulin A
immunoglobulin D
immunoglobulin E
immunoglobulin G
immunoglobulin M
haptoglobin
hemoglobin
ceruloplasmin
cholinesterase
hemopexin
myoglobin
rheumatoid factor
thyroxine-binding globulin
transferrin
transcortin
plasminogen
specific antibodies
coagulation factor

TABLE I-continued
ANALYTES

Microbial Surface Markers bacterial antigens
fungal antigens
parasitic antigens
viral antigens Cancer Cell Markers carcinoembryonic antigen
gangliosides

Cytolysins

A large number of cytolysins exist which may be employed with the present invention. These cytolytic agents are commonly of natural origin; however synthetic cytolysins such as surfactants and analogs of naturally occurring agents can also be used. Cytolysins are also commonly referred to as hemolysins when red blood cells are involved as the vesicle. Molecular weights generally are in the range of 100–2000 for many of the synthetic cytolysins and 2000–100,000 for some of the naturally occurring agents. Many naturally occurring cytolysins are polypeptides and proteins, such as melittin and streptolysin O, respectively, while others are typically classified as glycosides (e.g. saponin) or macrolides (e.g., polyene antibiotics). For the purpose of this invention, the term cytolysin includes the naturally occurring cytolysins, their derivatives, synthetic analogs, and synthetic cytolysins exemplified in Table II.

TABLE II
CYTOLYSINS

Aerolysin
Amphotericin B
*Aspergillis haemolysin*
Alamethicin
A-23187 (calcium ionophore)
Apolipoproteins
ATP Translocase
Cereolysin
Colicins
Detergents (Tritox ®, Brij ®, Cetrimides)
Direct lytic factors (from animal venoms)
Diptheria toxin
Filipin
Gramicidin
Hemolysins
Ionomycin
Listeriolysin
Melittin
Metridiolysin
Nigericin
Nystatin
Phospholipases
Polyene antibiotics
Polymyxin B
Saponin
Sodium fusidate
*Staphylococcus aureus* toxins ($\alpha,\beta,\gamma,\delta$)
Streptolysin O
Streptolysin S
Synexin
Surfactin
Tubulin
Valinomycin
Vibriolysin The preferred cytolysin of this invention is melittin, since it is commerically available, well characterized in terms of structure and function, and of low molecular weight. Melittin is a 26 amino acid polypeptide in which the amino acids are linked together to form substituted amide bonds with characteristic side chains with the following structure based upon standard nomenclature $H_2N$-GLY-ILE-GLY-ALA-VAL-LEU-LYS-VAL-LEU-THR-THR-GLY-LEU-PRO-ALA-LEU-ILE-SER-TRP-ILE-LYS-ARG-LYS-ARG-GLN-GLN-$CONH_2$.

Melittin is isolated from bee venom [E. Habermann, et al., Z. Physiol. Chem., Vol. 348, 37 (1967)] and has the demonstrated ability to lyse both erythrocytes and lipid vesicles [G. Sessu, et al., J. Biol. Chem., Vol. 244, 3575 (1969)]. The kinetics and mechanism for erythrocyte lysis by melittin have been described, and it is known to produce transient openings (or holes) in the erythrocyte membrane through which large probes, such as hemoglobin, can pass [W. F. De Grado, et al., Biophys. J., Vol. 37, 329 (1982)]. Binding of melittin to membranes occurs rapidly at low concentrations of this cytolysin and the lytic activity is considerably faster than that of complement protein used in the prior art. These properties are of particular interest for constructing a sensitive immunoassay as described in the present invention. The low molecular weight of melittin, 3000 daltons, is important since the small size of the molecule increases the likelihood that interaction of the analyte-melittin conjugate with binding agent will modulate its cytolysin activity.

Analyte-Cytolysin Conjugate

The present invention utilizes novel analyte-cytolysin conjugates which can be synthesized by covalently linking cytolysin materials with analytes. The term "analyte-cytolysin conjugate" also refers to analytes which are themselves cytolysins, and to cytolysins which are covalently linked either to derivatives of the analyte or to a binding analog of the analyte. Immunoassays for large molecular weight analytes, such as proteins, require that only one or more (but not all) binding sites be attached to the cytolysin. For this reason, peptides that are derived from an analyte protein may work as well in the present invention as the analyte proteins themselves. An immunoassay for digoxin is another case where a binding analog of the analyte (ouabain) works as well as the analyte itself since both contain common binding sites and are recognized by the same antidigoxin antibody.

Conditions for covalently attaching an analyte, including its derivatives and analogs, to a cytolysin depend upon the particular molecular architecture of both types of molecules. For the most part, cytolysins contain functional groups such as amines, amides, carboxyls, sulfhydryls, hydroxyls, aldehydes, and/or others, to which an analyte with its own appropriate functional groups could be attached directly or indirectly. The attachment chemistry may vary depending upon the functional groups involved, the number of analyte molecules to be bonded per cytolysin, and the desirability of including a spacer arm between the analyte and the cytolysin. The conjugate must retain the ability to react with binding agent of the analyte and to alter vesicle membrane permeability. For melittin, possible sites of attachement include the hydroxy group of the threonine and serine amino acid residues, the amino group of the lysine or N-terminal glycine residue, and the carbonyl group of the C-terminal glutamine residue of the polypeptide molecule.

In the case of the ouabain-melittin conjugate, a number of coupling chemistries are possible. Since hydroxyl groups are present upon two adjacent carbon atoms within the structure of ouabain, this material can be treated with sodium periodate to form two aldehyde groups. These groups can attach directly to the amino functionalities of melittin through a Schiff's base intermediate which can be reduced to a stable carbon-nitrogen bond. Such reduction can be carried out by conventional means such as either sodium borohydride or sodium cyanoborohydride. This sequence of reactions, commonly referred to as "periodate oxidation and borohydride reduction", results in an active conjugate which, when bound by antibody against digoxin, is no longer able to lyse vesicle membranes.

Alternatively, the analyte could be attached to the cytolysin through a spacer arm, such as 1,6-diaminohexane or other bifunctional crosslinking agents after periodate oxidation. The use of a spacer arm can facilitate the synthesis of the conjugate, or insure that the conjugate will possess the requisite immunochemical reactivity. For example, ouabain could be bonded through a spacer arm to the carboxyl terminal of melittin or to one of the amino groups if the appropriate crosslinking agent is used. A number of crosslinking agents, both homo and heterobifunctional, have been described in the literature [Pierce Bio-Research Products Technical Bulletin, "Double-Agents", Bifunctional Crosslinking Reagents, Pierce Chemical Co., Rockford, IL, U.S.A., 1982, Vol. 3] which could be used to couple ouabain to melittin. These crosslinking agents could be used with many different cytolysins and analytes of clinical importance. Carbodiimide crosslinking agents, such as 1-ethyl-3-(3-dimethylaminopropyl)carbodiimide, can also be employed to link analytes with carboxyl groups to amino groups on cytolysins or conversely, the amino groups of analytes to carboxyl groups on cytolysins.

The importance of binding analogs of the analyte is illustrated by the observation that ouabain-melittin conjugates have higher lytic activity at lower conjugate concentrations than does melittin alone. This type of behavior is expected for other analyte-cytolysin conjugates and would increase the sensitivity and range of utility of the resulting assay. The synthesis of conjugates incorporating binding analogs of the analyte can also provide an assay for the analyte despite difficulty in purifying the analyte-cytolysin conjugate, as for example with digoxin-melittin.

The chemical reactions involved in bonding analyte molecules, or their derivatives or analogs, to the melittin polypeptide or other cytolysin are known to those skilled in the art. The important features of a particular analyte-cytolysin conjugate are that the conjugate be stable under conditions of storage and use, i.e., that it not release analyte or analyte derivative or analog, that it react with binding agent specific for the analyte, and that it alter vesicle membrane permeability to release marker material. While covalent bonds have been found to insure these properties, bonding can involve other types of interactions which result in stable combinations of analyte and cytolysin, such as ionic or hydrophobic bonds. Such bonding methods are within the scope of this invention. Additionally, the molecular structure of the analyte derivative actually incorporated in the cytolysin to produce the conjugate can vary somewhat depending upon the particular bonding reactions to be utilized and possible use of a spacer arm. Such molecular structural variations to achieve bonding are not critical to characterize the analyte-cytolysin conjugate or to practice the invention. Thus "conjugate" means analyte molecule attached, directly or indirectly, to cytolysin molecule.

Antibody-Cytolysin Conjugate

One aspect of the present invention involves novel antibody-cytolysin conjugates which can be synthesized by covalently attaching cytolysin materials to antibody. Conditions for covalent attachment depend upon the particular molecular architecture of both types of molecules. For the most part, cytolysins contain functional groups such as amines, amides, carboxyls, sulfhydryls, hydroxyls, aldehydes, etc. to which an antibody with its own appropriate functional groups could be attached directly or indirectly. The attachment chemistry will vary depending upon the functional groups involved and the desirability of including a spacer arm.

Any number of methods can be employed to attach the cytolysin to the antibody. In general, at least one cytolysin label should be coupled to each antibody. The free sulfhydryl groups present on Fab′ fragments and the S-sulfonate group present on half-molecules (heavy chain-light chain dimers) provide specific reactive groups for covalent attachment of the cytolysin. Labeling of these groups is known not to affect the immunoreactivity of the antibody. Heterobifunctional crosslinking reagents having maleimido- or thiopyridyl- groups are useful for this purpose. Generally, it is desirable that the final step in the synthesis of the labeled antibody be an immunopurification step to ensure retention of immunoreactivity.

In any event, the antibody must retain its ability to recognize and immunochemically bind to the analyte, and the cytolysin must retain its ability to alter vesicle membrane permeability. The use of whole antibody, Fab, Fab′ and half-molecules is contemplated as being within the scope of the present invention. It is believed that the greatest sensitivity will be achieved using a monovalent antibody.

Monovalent antibodies are produced by known methods. For example, Fab fragments are obtained by papain digestion of IgG; Fab′ fragments are obtained by disulfide reduction of $F(ab')_2$ fragments obtained by pepsin digestion of IgG; half-molecules are formed by sulfitolysis of IgG as described in pending U.S. patent application Ser. No. 374,971 filed May 5, 1982 and incorporated herein by reference. Intact IgG is sulfitolyzed with sodium sulfite (100mM per mg of IgG) in the presence of 5,5′-dithiobis(2-nitrobenzoic acid) (2.5mM per mg IgG), preferably in a buffered medium at room temperature under nitrogen, to yield S-sulfonated half-molecules of IgG. In general, it will be desirable to immunopurify the antibody prior to its use in an immunoassay. Again, the methods for isolation of IgG from animal serum and the methods for its immunopurification by affinity chromatography are known.

Binding Agents

Analytes (as well as analyte-cytolysin conjugates) and their specific binding agents rapidly interact and combine to form a tightly bound complex. Antisera for the analytes shown above are known. Generally, the smaller analytes (molecular weight less than 5000 daltons) are haptenated (covalently conjugated in immunologically active form), to proteins like human or bovine serum albumin to produce an immunogen. The antibody can be used in this assay as a serum fraction, a partially purified immunoglobulin fraction, as an immunopurified monospecific antibody fraction, or as monoclonal antibody. The preparation of these various antibody fractions are well known in the literature. [Weir, D. M., Handbook of Experimental Immunology, Blackwell Science Publication, Oxford 1978, pp. 6.1 to 10.5.]

For some analytes, specific binding agents can be substituted for specific antibodies in these assays. For example, physiological hormone-receptors extracted from tissue homogenates can be used in place of antibodies to detect and quantify hormones. For glycoproteins, specific plant or animal lectins can be used. Similar binding agents also exist for many vitamins (e.g., avidin/biotin and vitamin $B_{12}$/intrinsic factor) which exhibit very high affinity. Such nonantibody binding agents are advantageous in that they are naturally occurring, generally monovalent, and have high affinity and specificity.

Vesicles and Marker Materials

There are several methods for the preparation of artificial phospholipid vesicles. As will be appreciated, it is important that the method utilized be simple, reproducible, produce large (>1000 Å diameter) unilamellar vesicles and not employ conditions that will inactivate the marker system (e.g., enzyme) to be sequestered. Of the methods that have been reported, the detergent removal procedure [Mimms, L. T., et al., Biochem., Vol. 20, 833–840 (1981); Helenius, A., J. Cell. Biol., Vol. 75, 866–880 (1977); and Brunner, J., et al., Biochem. Biophys. Acta, Vol. 455, 322–331 (1976)] meets the aforementioned requirements. The detergent octyl glucoside is reported to produce vesicles of 1500–2000 Å in diameter and was found to be compatible with β-galactosidase and alkaline phosphatase, enzymes which have been utilized as sequestered marker materials.

In the preferred embodiment, single wall lipid vesicles of 1500 Å (diameter) are prepared by detergent removal. Egg lecithin dissolved in chloroform-methanol along with cholesterol dissolved in chloroform are dried to a thin film under a stream of argon. Organic solvent is removed by vacuum drying. The phospholipid-cholesterol film is solubilized in octyl β-glucopyranoside by vigorous mixing at room temperature. The marker material to be sequestered is then added either in dry form (e.g., 5–10 mg of alkaline phosphatase) or in liquid form (smallest volume possible). The mixture is then dialyzed against multiple changes of Tris.HCl. The solution is then chromatographed on a Sepharose 4B-CL column to remove residual detergent and to fractionate vesicles with sequestered marker from free marker material. All procedures are carried out with argon-flushed buffers. Vesicles eluting in the void volume of the column are pooled and stored at 4° C. under argon. The vesicle peak is identified both by monitoring the eluant for absorbance at 280 nm and for radioactivity ($^{14}C$-phosphatidylcholine added as a vesicle identification marker).

The vesicles prepared in this fashion have a mean diameter of about 1500 Å when examined by negative stain electron microscopy. The internal volume of these vesicles calculated from the measured diameter is about $1.5\times10^{-15}$ ml.

The stability of these vesicles to storage at 4° C. can be examined by measuring the amount of alkaline phosphatase activity measured prior to and after the addition of excess detergent (0.1% Brij-58), as a function of time (Table III). To do this, 50 fmols (femtomoles$=10^{-15}$ moles) of phospholipid vesicles are added to a 2 ml solution of 2mM o-nitrophenyl phosphate, 0.05M Tris.HCl (pH 7.8). The enzyme activity is measured kinetically on a recording spectrophotometer at 410 nm. As shown in Table III, the percentage of the enzyme activity remaining encapsulated is virtually unchanged over a four-month period. The vesicles are stored at a concentration of 5mM lipid in 50mM Tris.HCl, pH 7.8, under an atmosphere of argon. When cholesterol is omitted as a vesicle constituent, a leakage rate of about 7% per month is observed for sequestered 6-carboxyfluorescein or alkaline phosphatase.

TABLE III
VESICLE STABILITY

| Length of Storage at 4° C. | Percentage of Enzyme Activity Encapsulated |
| --- | --- |
| Day 1 | 94.2 |
| Day 14 | 94.3 |
| Day 21 | 94.2 |
| Day 28 | 94.6 |
| Day 35 | 94.6 |
| Day 49 | 94.6 |
| Day 56 | 94.6 |
| Day 87 | 92.6 |
| Day 117 | 94.0 |

Alternate vesicle formation procedures can also be used to sequester various marker systems. Details of these possible procedures are given in the literature [Batzri, S., et al., Biochem. Biophys. Acta, Vol. 298, 1015–1019 (1973); Zumbudhl, O., et al., Biochem. Biophys. Acta, Vol. 640, 252–262 (1981); Kim, S. et al., Biochem., Biophys. Acta, Vol. 646, 1–9 (1981); and Szoka, F., et al., PNAS, Vol. 75, 4194–4198 (1978)]. It should be recognized that red blood cells and red blood cell ghosts can be used instead of artificially formed vesicles [DeGrado, W. F., et al., Biophys, J., Vol. 37, 329–338 (1982)]. For example, when using red blood cells, lysis by the analyte-cytolysin conjugate can be monitored by following the release of hemoglobin or other internal substances. Furthermore, electrodes containing lipid structures can also be used in conjunction with the analyte-cytolysin technology, since thin films of lipid can be perturbed by melittin [Kempf, C., et al., Biochemistry, Vol. 257, 2469–2476 (1982)] and stable lipid films for electrochemical sensors have been described for valinomycin and amphotericin B [Thompson, M., et al., Anal. Chim. Acta, Vol. 117, 133–145 (1980)].

Table IV lists some potential marker systems that can be sequestered within the lipid vesicles. The mode of detection of the marker upon release is also indicated in Table IV. The two major criteria to be met by a marker system are (1) the vesicle membrane must be relatively impermeable to the sequestered marker, and (2) the sequestered marker must not be detectable until released from within the internal space of the lipid vesicles and allowed to mix with the external milieu, or in the case of a sequestered enzyme system, until substrate diffuses into the vesicle as a result of an alternation in membrane permeability and is converted to a detectable form.

TABLE IV
DETECTABLE MARKER SYSTEMS

| Sequestered Material | Detection Mode |
| --- | --- |
| Enzymes | Enzyme activity coupled to colorimetric, fluorometric, luminescent, electrosensing, potentiometric measurements |
| Substrates or cofactors | Same as above |
| Fluorophores (self-quenching or in combination with quencher) | fluorometry |
| Chromophores (self-quenching) | Absorbance |
| Spin labels | ESR/EPR |
| Ions | Ion-selective electrodes |

Assay Method

The preferred method of conducting an assay is as follows: A known volume (5 μl to 500 μl) of sample containing the analyte to be measured (preferably 5 μl) is added to 1 to 5 ml of buffered solution (preferably 2 ml of 50 μM Tris.HCl, pH 7.8). If the marker system is an enzyme, this buffered solution should also contain substrate (e.g., the solution would contain 2 μM p-nitrophenyl phosphate when alkaline phosphatase is sequestered within the vesicles). A known amount of antibody or binding agent (preferably an amount approximately twice the suspected molar amount of unknown analyte) in the form of whole antiserum, an IgG-fraction, or as affinity-purified monospecific antibody is added. The volume of antibody solution should preferably be relatively small in comparison to the total assay volume (<5%). After a brief preincubation period at a controlled temperature (preferably 5–15 minutes at 37° C.) a known amount of analyte-cytolysin conjugate is added. The amount of analyte-cytolysin conjugate added should be approximately equal to the molar amount of antibody or binding agent used. After another brief incubation period at a controlled temperature (preferably 5–15 minutes at 37° C.) an amount of lipid vesicles known to be in excess (preferably 10–100 femtomoles) containing a sequestered marker system is added. The greater the amount of analyte present in the sample, the more extensive the lysis by the analyte-cytolysin conjugate. Release of the marker system is quantified by a convenient detection system. For sequestered alkaline phosphatase, the conversion of substrate by enzyme is monitored continuously by a recording spectrophotometer by following the production of color (p-nitrophenolate anion) at 410 nm. As shown by FIG. 1, the greater the concentration of free digoxin in the assay system, the greater the amount of unbound ouabain-melittin conjugate available for interaction with vesicles which results in an increased enzymatic activity as monitored by substrate conversion.

It must also be appreciated that the order of addition of the various reagents can be altered without seriously compromising the asssay results. The order of addition described here, however, was found to be optimal when using the reagents cited. When red blood cells or red blood cell ghosts are used instead of artificial lipid vesicles, the method of assay is essentially the same. Hemolysis can be readily monitored spectrophotometrically by procedures well known in the art.

For convenience, quickness, and increased accuracy of testing, the present invention can be used on automated analytical instruments such as the Du Pont aca ™ discrete clinical analyzer with its analytical test packs (U.S. Pat. No. Re. 29,725). In this application, reagents such as antibody, analyte-cytolysin conjugate, vesicles containing marker material would be packaged separately in breakable compartments of an analytical test pack that is composed of pliable material. The aca ™ analyzer would automatically conduct the analysis by taking the sequential steps of (1) recognizing the particular test to be performed; (2) dispensing a programmed volume of biological sample containing analyte into the analytical test pack; (3) adding a programmed volume of buffer; (4) releasing antibody, analyte-cytolysin, and vesicle reagents from compartments to contact sample; (5) mixing reagents and sample; (6) incubating the reaction mixture; (7) releasing enzyme substrate from its compartment to contact the reaction mixture; (8) mixing again; (9) measuring the rate or amount of enzyme released from vesicles; (10) converting the amount of enzyme released into concentration units of analyte using a preprogrammed mathematical transform; and (11) displaying the result to the instrument operator. The total time for analysis of a sample would be less than eight minutes, and successive samples could be processed at one-minute intervals or less. Analyte-cytolysin conjugates containing melittin are well suited for this type of automated procedure since the rate of vesicle lysis is rapid, producing measurable levels of released enzyme within seconds after mixing. On the other hand, assays requiring complement [Haga, et al., Biochem. Biophys. Res. Commun., 95, 187-192 (1980)] are not as easily automated since the kinetics of vesicle lysis are considerably slower requiring a thirty-minute incubation time.

EXAMPLES

Unless specified otherwise, in all statements of assay conditions and preparation of reagents, temperature is expressed in °C., concentrations referred to as percentages are by weight/volume, and abbreviations utilized are: ml (milliliter), l (liter), gm (gram), mol (mole), mmol (millimole), mg (milligram), $\mu$C (microCurie), mA (millAbsorbance).

EXAMPLE 1a

Production and Purification of Anti-Digoxin Antibody

Antiserum to digoxin was raised in rabbits by immunization with a digoxin-bovine serum albumin (BSA) conjugate. The synthesis of the digoxin-albumin conjugate is described by Smith, et al. [Biochem. Biophys. Acta, Vol. 684, 197-194 (1982)]. Digoxin (436 mg) suspended in 20 ml of absolute ethanol, was oxidized by the addition of 20 ml of 0.1M sodium metaperiodate at room temperature. After 1 hour, the reaction was stopped by consuming the excess periodate with the addition of 0.6 ml of 1M glycerol. Thirty minutes later, the reaction mixture was added dropwise to 560 mg of bovine serum albumin dissolved in 20 ml of water which had been adjusted to pH 9.5 with 0.4 ml of 5% $K_2CO_3$. One hour later, 0.3 gm of sodium borohydride, freshly dissolved in 20 ml of water, was added. Three hours later, 7.6 ml of 1M formic acid was added to lower the pH to 6.5. After 1 hour at pH 6.5, the pH was raised to 8.5 with the addition of 1.5 ml of 1M NH$_4$OH. The entire reaction mixture was then dialyzed against 5 changes (16 l each) of distilled water followed by one change (16 l) of 0.015M sodium phosphate, pH 7.8. The albumin-conjugated digoxin was provided to Cappel Laboratories, West Chester, Pa., for the production of antiserum by procedures well known in the art.

Antibodies specific to digoxin were purified from the whole rabbit antiserum obtained from Cappel Laboratories in one step using affinity column chromatography. The affinity resin was composed of a digoxin derivative (ouabain) immobilied on an agarose matrix.

EXAMPLE 1b

Synthesis of Ouabain Affinity Resin

Ouabin was attached to an agarose matrix through a protein (human serum albumin, HSA) spacer arm. The first step involved the synthesis of a ouabain-HSA conjugate. Ouabain (0.56 mmol dissolved in 20 ml of water) was oxidized with sodium metaperiodate (1.02 mmol) for 1 hour at room temperature in the dark. Quantitative oxidation was verified by thin layer chromatography on silica gel G plates developed in ethylacetate:methanol:-H$_2$O (75:25:1 v/v). The excess periodate was removed by passing the aqueous mixture over a 3 ml column of DOWEX AG-1X8, a strong basic anion exchange resin with quaternary ammonium exchange groups attached to a styrene divinyl benzene copolymer lattice. Quantitative recovery of ouabain was verified by following radiolabeled (tritiated) ouabain. The solution of oxidized ouabain was buffered to pH 9.5 with the addition of 0.4 ml of 5% Na$_2$CO$_3$, and combined with 20 ml of HSA solution (28 mg/ml). After 45 minutes, the conjugate was reduced with the addition of 0.3 gm of sodium borohydride freshly dissolved in 20 ml of water. Three hours later, 8 ml of 1M formic acid was added to lower the pH to 6.5. After 1 hour at pH 6.5, the pH was raised to pH 7.5 with 1M NH$_4$OH. The entire reaction mixture was dialyzed exhaustively against distilled water, and then finally against 0.015 M sodium phosphate buffer, pH 7.8, 0.15M NaCl. The conjugate was concentrated on an Amicon PM-30 membrane. The final product was 4.2 mg/ml in protein, assayed by the method of Lowry [Lowry, O. A., et al., J. Biol. Chem., Vol. 193, 265-275 (1951)] with a ouabain-to-HSA molar ratio of 5 [ouabain assayed by the cardiac glycoside colorimetric assay of Forbush, B., et al., Biochemistry, Vol. 17, 3668-3676 (1978)]).

The ouabain-HSA conjugate was immobilized on Affi-Gel ®10 (Bio-Rad Laboratories), a beaded cross-linked agarose support with a 10 carbon atom neutral spacer arm terminating in N-hydroxysuccinimidyl ester for coupling, proteins and other molecules through amino groups, using the procedure described in the Bio-Rad manual. In this procedure, 25 ml of Affi-Gel ®10 was washed with 75 ml of ice-cold isopropanol and then 75 ml of ice-cold water. The gel was added to the dialyzed ouabain-HSA conjugate and allowed to mix on a rocker overnight at 4° C. The excess active ester groups were quenched by adding 0.1 ml of 1M ethanolamine, pH 8.0, for 1 hour at room temperature. Finally, the gel was washed extensively with distilled water, and then in turn: 500 ml of 0.5M NaCl; 400 ml of 0.1M glycine, pH 2.5; 300 ml 2.5M NH$_4$SCN; 1000 ml phosphate buffered saline which consists of 0.15M NaCl, 0.015M sodium phosphate, at pH 7.4. The resin was stored at 4° C. in the presence of 0.02% sodium azide.

EXAMPLE 1c

Affinity Column Chromatographic Purification

Digoxin-specific antibodies were immunopurified directly from whole rabbit serum by affinity column chromatography. The ouabain affinity resin of Example 1b was packed into a column (0.7×15 cm) to a bed volume of 6 ml and equilibrated with phosphate-buffered saline. Antiserum (10 ml of Cappel α-digoxin serum at 4.5 mg/ml monospecific antibody) was applied at a flow rate of <1 ml per minute. The column was washed with phosphate-buffered saline until the absorbance at 280 nm reached baseline (<0.01). Antibody was then eluted from the column with 60 ml of 3M NH$_4$SCN (pH 7.5) and immediately dialyzed against 4×two liter changes of phosphate-buffered saline at 4° C.

EXAMPLE 1d

Synthesis of Ouabain-Melittin Conjugate

Ouabain was coupled through its sugar moiety to the lysine ε-amino groups of melittin. The reaction sequence involved is very similar to that described previously for the synthesis of digoxin and ouabain albumin conjugates. 200 μmol of ouabain plus 10 μC of ($^3$H)-ouabain dissolved in 10 ml of water was oxidized by the addition of 600 μmol of sodium metaperiodate for 60 minutes at 25° C. Excess periodate was then removed by passing the mixture through a column containing 3-ml Dowex 1-X8(Cl), a strong anion exchange resin with quaternary ammonium exchange groups attached to a styrene divinylbenzene copolymer lattice. The oxidized ouabain solution was made 0.1M in phosphate, pH 6.5, by the addition of 1 ml of 1M sodium phosphate, pH 6.5. Melittin (10 mg) was then added as a solid. After 1 hour at 25° C., 100 μmol of sodium cyanoborohydride (6.28 mg) was added and the pH of the solution readjusted to 6.5. The coupling was allowed to proceed with mixing at 25° C. for 3 days. During this time, a large precipitate was observed. The precipitate was separated from the supernatant by brief centrifugation at 10,000×g. The supernatant which contained no protein (as determined by U.V. spectrum), but approximately 50% of the ($^3$H)-ouabain, was discarded. The precipitate was washed once with 10 ml of ice-cold water and collected by centrifugation. Finally, the precipitate was dissolved in 2 ml of 0.1M sodium acetate buffer, pH 4.5, and chromatographed on a 1.5×40 cm column containing Sephadex G-25, a crosslinked beaded dextran for gel permeation chromatography, equilibrated in the same buffer. A single protein peak eluted in the void volume of the column. Ultraviolet spectrum of this peak clearly showed an altered spectrum from that exhibited by native melittin. Measurement of radiolabeled ouabain indicated that the conjugate contained, on the average, three ouabain molecules per melittin molecule.

Example 1e

Lipid Vesicle Formation

Single wall lipid vesicles of 1500 Å diameter were prepared by a modified detergent removal procedure similar to that described in the literature [Mimms, L. T., et al., Biochemistry, Vol. 20, 833–840 (1980)]. Egg lecithin (2.4×10$^{-5}$ mol) dissolved in 176 μl of 2:1 (v/v) chloroform-methanol along with cholesterol (1.2×10$^{-5}$ mol) dissolved in 44 μl of chloroform were dried to a thin film under a stream of argon in a 10 ml borosilicate glass test tube. Residual traces of organic solvent were removed by vacuum drying for 3≠4 hours. The phospholipid-cholesterol film was solubilized in 3.75 ml of 200mM octyl β-D-glucopyranoside by vigorous mixing at room temperature. Ten mg of lyophilized alkaline phosphatase was then dissolved in the solution of lipid and detergent. This mixture was immediately dialyzed against two 2 liter changes of 0.05M Tris.HCl, pH 7.8, at 25° C. After this, the solution was chromatographed on a 1.5×40 cm column containing Sepharose 4B-CL, crosslinked macroporous agarose in bead form for gel permeation chromatography, equilibrated in 0.05M Tris.HCL, pH 7.8, to remove residual detergent and to fractionate vesicles with entrapped enzyme from free enzyme. All procedures were carried out with argon-flushed buffers. Vesicles eluting in the void volume of the column were pooled and stored at 4° C. under argon. The vesicle peak was identified both by monitoring the eluant for absorbance at 280 nm and radioactivity ($^{14}$C-phosphatidylchlorine).

The vesicles prepared in this fashion eluted in the void volume of the Sepharose 4B-Cl column and were determined to have a mean diamter of about 1500 Å when examined by negative stain electron microscopy. From the internal volume of these vesicles (1.5×10$^{-15}$ ml) and the concentration of enzyme (alkaline phosphatase) in the dialysis mixture, it can be calculated that there are about 14 molecules of alkaline phosphatase sequestered per vesicle. This value agreed very well with the experimental data in which the alkaline phosphatase activity eluting in the column void volume was measured before and after total lysis of the vesicles with detergent. The vesicles were stored at a concentration of 5mM lipid in 50mM Tris HCl, pH 7.8, under an atmosphere of argon.

Other enzymes, e.g., β-galactosidase, can be encapsulated in lipid vesicles. Eighty-eight microliters of egg yolk lecithin (100 mg/ml lipid in chloroform: methanol (2:1)) was dried in the bottom of a test tube under a stream of argon. Remaining traces of organic solvent were removed by lyophilization. The lipid was dissolved in 600 μl of 200 octyl-62-D-glucopyranoside by vigorous mixing. To this lipid-detergent mixture was added 200 μl of a β-galactosidase solution at 3.2 mg/ml protein. Immediately thereafter, the sample was chromatographed on a Sephadex G-25 column (1.5×40 cm) equilibrated in 10mM Tris.HCl, pH 7.6. The void volume fractions containing the lipid vesicles were pooled and rechromatographed on a Sapharose 4B-Cl column (1.5×40 cm) to remove unencapsulated enzyme. The lipid vesicles containing the entrapped β-galactosidase eluting in the void volume of the column were pooled and stored at 4° C. under argon.

The release of β-galactosidase from the lipid vesicles upon lysis by either detergent or melittin was monitored by measuring the enzyme activity. For this, 50 μl of vesicles containing entrapped β-galactosidase was diluted into 1.5 ml of 0.15M sodium phosppate, pH 7.4 containing 2.5mM o-nitrophenyl-galactopyranoside at 37° C. After recording the blank enzyme rate, a small amount of detergent (5 μl of 20% Triton-X-100) or melittin (50mM) is added and the enzyme activity monitored again by following the change in absorbance at 405 nm.

Another marker material which can be sequestered within lipid vesicles is 6-carboxyfluorescein. Eighty-eight microliters of egg yolk lecithin (100 mg/ml lipid in chloroform:methanol (2:1) was dried down in the bottom of a test tube under a stream of argon. Excess organic solvent was removed by lyophilization overnight. The lipid was dissolved in 600 μl of 200mM β-D-octylglucoside by vigorous mixing. The lipid-detergent mixture was fractionated through a Sephadex G-25 column (1.5×40 cm) equilibrated in 10mM Tris.HCL, pH 7.6, 60mM NaCl to remove excess detergent and unincorporated 6-carboxyfluorescein. The void volume fractions contained the lipid vesicles with entrapped 6-carboxyfluorescein as identified by monitoring the absorbance at 473 nm. The vesicles were immediately stored at 4° C. under argon.

The release of 6-carboxyfluorescein from the lipid vesicles upon lysis by either detergent or cytolysin (melittin) was monitored by measuring the fluorescence enhancement. Twenty microliters of the vesicle fraction was diluted into 2 ml of 0.15M NaCl, 0.015M sodium phosphate, pH 7.4. The steady state fluorescence was then recorded by exciting at 493 nm and measuring the emission at 519 nm. Addition of excess detergent (0.2% final concentration) or melittin (as little as 20 nanomolar) results in a 3-4 fold increase in fluorescence intensity of the 6-carboxyfluorescein. Vesicle stability was monitored for 28 days with an observed leak rate of 7% 6-carboxyfluorescein released per month.

EXAMPLE 1f

Homogeneous Digoxin Assay

Measurements were performed in a total assay volume of 2 ml of 0.05M Tris HCl, pH 7.8 containing 2 mM p-nitrophenyl phosphate at 37° C. A standard stock solution of digoxin was prepared by dissolving digoxin in dimethylformamide at a concentration of 1 mg/ml. A working dilution of this digoxin stock solution was prepared by dilution to 10 μg/ml and 1 μg/ml with 0.05M Tris.HCl, pH 7.8. Final concentrations of 1, 5, and 10 ng/ml digoxin in the assay buffer were achieved by adding 2 μl, 10 μl, and 20 μl of the 1 μg/ml digoxin to the 2 ml assay solutions, respectively. A final concentration of 100 ng/ml was obtained by adding 20 μl of the 10 μg/ml digoxin standard to the 2-ml assay volume and the 1000 ng/ml sample was obtained by adding 2 μl of the mg/ml digoxin stock solution to 2 ml of assay buffer. After the addition of digoxin, 25 μl of affinity-purified digoxin antibodies at $6.24 \times 10^{-6}$M in phosphate buffered saline were added. Following a one minute preincubation period, 5 μl of a $7.8 \times 10^{-6}$M solution of ouabain-melittin conjugate, as prepared in Example 1d, dissolved in 0.1M sodium acetate, pH 4.5 was added. Following another preincubation period of five minutes, 12 μl of a 50mM lipid vesicle solution with sequestered alkaline phosphatase in 50mM Tris.HCl, pH 7.8 was added. The absorbancy of this solution was continuously monitored at 410 nm. The kinetic rate of the released enzyme activity (ΔA410/min) is plotted by a function of final digoxin concentration in the assay mixture as shown in the FIG. 1.

EXAMPLE 2a

Synthesis of Melittin-Biotin Conjugate

Melittin (1.7 mg) was dissolved in 2 ml of 0.15M sodium phosphate, pH 7.8. To this solution was added 5 mg of N-hydroxysuccinimidobiotin, available commercially from a number of suppliers, and the biotinylation reaction was allowed to proceed at 25° C. for 2 hours. During this time, a large precipitate formed. The precipitate was collected by contrifugation and then dissolved in 1.5 ml of 0.1M sodium acetate buffer, pH 5.6. This sample was then chromatographed on a Sephadex G-25 column (1.5×40 cm) equilibrated in 0.1M sodium acetate, pH 5.6. The melittin-biotin conjugate was identified in the column eluate by monitoring the absorbance at 280 nm. The peak fractions were pooled and stored at 4° C.

EXAMPLE 2b

Biotin Assay

Vesicles containing entrapped alkaline phosphatase were formed as described in Example 1e. Assays were performed in a total assay volume of 2 mL of 0.05M Tris.HCl, pH 7.8, containing 2mM p-nitrophenylphosphate at 37° C. Free biotin was added to the assay mixtures at concentrations of 0, 0.5, 1, 2, 5, and 10 ng/ml followed by 2 μl of a 1 mg/ml avidin stock solution (final concentration of avidin was $1.7 \times 10^{-8}$M). After 2 minutes at 37° C., 25 μl of the melittin-biotin conjugate was added (final concentration about $1 \times 10^{-7}$M). Five minutes later, 10 μl of preformed phospholipid vesicles containing entrapped alkaline phosphatase was added and the release of enzyme was followed by monitoring the absorbance change at 410 nm. A plot of enzyme activity versus final biotin concentration in the assay is shown in FIG. 2. Maximum signal was determined by adding 5 ml of a 20% Brij-58 solution to the assay.

EXAMPLE 3a

Synthesis of Melittin-Antibody Conjugate

Monospecific antibodies to the analyte of interest are obtained from high affinity antiserum by affinity chromatography. The procedure for doing this is well known in the art on a specific example is described above in Example 1c. The purified F(ab')2 fraction is obtained using pepsin digestion and subsequent column chromatography. This methodology is also well known in the art. Briefly, 20 mg of affinity-purified antibodies dissolved in 2 ml of 0.1M sodium acetate buffer, pH 4.5, are digested with 200 μg of pepsin for 16 hours at 37° C. The sample is clarified by centrifugation and then chromatographed on a 1.5×90 cm column containing Sephadex G-150, a crosslinked beaded dextran for gel permeation chromatography, equilibrated in 0.015M sodium phosphate, pH 7.4, 0.15M NaCl. The column fractions containing the F(ab')2 fragments, identified by gel electrophoresis, are pooled and reconcentrated to 2 ml by pressure filtration. The F(ab')2 fragments are then converted to their corresponding monovalent Fab'-fragments by reductive cleavage with dithiothreitol. To do this, the solution of F(ab')2-fragments from above are made 20mM in dithiothreitol and allowed to incubate at 25° C. for 1½ hours uner an atmosphere of argon. Excess dithiothreitol is removed by dialysis against 0.1M sodium phosphate, pH 5.6 at 4° C.

The Fab'-fragments are coupled to melittin using the heterobifunctional crosslinking agent m-maleimidobenzoyl N-hydroxysuccinimide ester (MBS, purchased from Pierce Chemicals). In this way the amino residues of melittin are acylated by the active N-hydroxy-succinimidyl ester of MBS to form a covalent adduct, and then the free sulfhydryl groups on the Fab'-fragments form a covalent adduct with the maleimidyl moiety of MBS.

For this, 2 mg of melittin ($6.7 \times 10^{-7}$ mols) dissolved in 1 ml of phosphate buffered saline, pH 7.0, is mixed with 42 μl of 79.6mM MBS (dissolved in tetrahydrofuran) for 60 minutes at 25° C. The reaction is stopped and reaction products are removed by desalting the mixture on a Sephadex G-25 column (1.5×40 cm) equilibrated in phosphate buffered saline. The derivatized melittin fractions which elute from the column are combined with the Fab'-SH fraction, the pH of the solution readjusted to pH 7.5, and allowed to incubate with mixing at 4° C. After 16–20 hours the Fab'-melittin conjugate is purified by column chromatography using Sephadex G-100.

EXAMPLE 3b

Heterogeneous Assay

In the preferred mode, the heterogeneous assay using the antibody-cytolysin conjugate is performed as follows. A known volume of patient sample, usually 5 μl to 500 μl, containing an unknown amount of analyte is mixed with a solution containing an amount of monovalent antibody-cytolysin conjugate known to be in excess over analyte. Usually the conjugate will be present in approximately 100-fold molar excess over analyte. Analyte and conjugate are preincubated for a specific length of time, usually at least 5 minutes and not more than 30 minutes, at a fixed temperature between 4° C. and 45° C., usually 22°–25° C. A known volume (usually 5 μl to 500 μl) of this solution containing analyte and conjugate is passed through a column, preferably of dimensions 2 mm×10 mm, consisting of analyte or analyte-analog immobilized on a porous support. Sufficient analyte-coupled (or analyte-analogue-coupled) support must be used to bind preferably all of the free conjugate. The column is eluted at a flow rate of 0.2–5.0 ml per minuted with a suitable buffer, usually 1–5 ml total volume. The fraction which elutes from the column contains conjugate complexed with analyte from patient serum.

A suspension of vesicles containing marker material is added to this fraction. As the cytolysins reacts with the lipid vesicle, the permeability of the vesicles will increase, thereby releasing the marker material into the external milieu, thereby allowing the marker material to be detected.

It will be apparent that the instant specification and examples are set forth by way of illustration and not limitation, and that various modifications and changes may be made without departing from the spirit and scope of the present invention.

What is claimed is:

1. A conjugate for the detection of an analyte in a test sample, comprising in combination:
    (1) cytolysin means for altering the permeability of a membrane of a vesicle, said means being conjugated to
    (2) at least one analyte molecule.

2. The conjugate of claim 1 wherein the cytolysin is selected from the group consisting of aerolysin, amphotericin B, alamethicin, A-23187 (calcium ionophore), ATP translocase, cereolysin, diptheria toxin, filipin, gramicidin, melittin, nigericin, nystatin, polymyxin B, *Staphylococcus aureus* toxin α, β, γ, or δ, Streptolysin O, Streptolysin S, tubulin and valinomycin.

3. The conjugate of claim 1 wherein the cytolysin is melittin.

4. The conjugate of claim 3 wherein the attachment of analyte derivative is through an amino acid residue selected from the group consisting of lysine, serine, threonine, N-terminal glycine, and C-terminal glutamine.

5. The conjugate of claim 1 wherein the analyte derivative is a drug, metabolite, hormone, steroid, pesticide, environmental pollutant, food toxin, vitamin, protein, microbial surface marker, cancer cell marker, fungus, protozoan, virus, cell or tissue antigen.

6. The conjugate of claim 5 wherein the analyte derivative is a drug.

7. The conjugate of claim 6 wherein the drug is ouabain.

8. The conjugate of claim 4 wherein at least one ouabain molecule is attached to melittin through an ε-amino group of a lysine residue.

9. The conjugate of claim 5 wherein the analyte derivative is a vitamin.

10. The conjugate of claim 9 wherein the vitamin is biotin.

11. The conjugate of claim 4 wherein at least one biotin derivative molecule is attached to melittin through an ε-amino group of a lysine residue.

12. An analyte-cytolysin conjugate comprising a substituted melittin molecule of the formula:

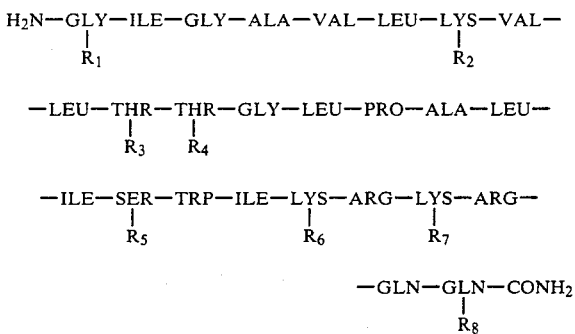

wherein at least one of $R_1$ through $R_8$ is an analyte derivative molecule selected from the group consisting of drug, vitamin, hormone, metabolite, steroid, pesticide, environmental pollutant, food toxin, protein, microbial surface marker, cancer cell marker, fungus, protozoan, cell or tissue antigen, provided that when at least one of $R_2$, $R_6$, or $R_7$ is said analyte derivative, attachment is through an ε-amino group of the amino acid side chain; when at least one of $R_3$, $R_4$, or $R_5$ is said analyte derivative, attachment is through a hydroxyl group of said amino acid side chain; when $R_1$ is said analyte derivative, attachment is through the N-terminal amino group; and when $R_8$ is said analyte derivative, attachment is through the C-terminal carboxyl group.

13. The conjugate of claim 12 wherein at least one of $R_2$, $R_6$, or $R_7$ is a ouabain derivative.

14. The conjugate of claim 12 wherein at least one of $R_2$, $R_6$, or $R_7$ is a biotin derivative.

15. A method for determining the amount of an analyte in liquid medium comprising the steps of:
    (A) forming a reaction system by contacting said liquid medium with
        (1) analyte specific binding agent;
        (2) analyte-cytolysin conjugate; and
        (3) vesicles containing marker material sequestered within the vesicle
    in proportions such that the interaction of unbound analyte-cytolysin conjugate with said vesicles results in the release of said marker material; and (B) measuring said marker material thereby released which is related to the amount of said analyte initially present in said liquid medium.

16. The method of claim 15 wherein the analyte is a drug, metabolite, hormone, steroid, pesticide, environmental pollutant, food toxin, vitamin, protein, microbial surface marker, cancer cell marker, fungus, protozoan, virus, cell or tissue antigen.

17. The method of claim 15 wherein the analyte is a drug.

18. The method of claim 17 wherein the drug is digoxin.

19. The method of claim 15 wherein the analyte is a vitamin.

20. The method of claim 19 wherein the vitamin is biotin.

21. The method of claim 15 wherein the analyte binding agent is selected from the group consisting of antibody, hormone-receptor, lectin, and specific binding protein.

22. The method of claim 21 wherein the binding agent is an antibody.

23. The method of claim 22 wherein the antibody is specific for digoxin.

24. The method of claim 21 wherein the binding agent is a specific binding protein.

25. The method of claim 24 wherein the specific binding protein is avidin.

26. The method of claim 15 wherein the analyte-cytolysin conjugate is ouabain-melittin.

27. The method of claim 15 wherein the analyte-cytolysin conjugate is biotin-melittin.

28. The method of claim 15 wherein the vesicle utilized to sequester marker material is selected from the group consisting of lipid vesicle, red blood cell, and red blood cell ghost.

29. The method of claim 28 wherein the vesicle is a lipid vesicle.

30. The method of claim 15 wherein the marker material is a substance selected from the group consisting of enzyme, cofactor, chromophore, fluorophore, spin label, and ion.

31. The method of claim 29 wherein the marker material is an enzyme.

32. The method of claim 30 wherein the enzyme is alkaline phosphatase.

33. The method of claim 30 wherein the enzyme is β-galactosidase.

34. The method of claim 30 wherein the fluorophore is 6-carboxyfluorescein.

35. A method for determining the amount of digoxin in liquid medium comprising the steps of:
(A) forming a reaction system by contacting said liquid medium with (1) digoxin specific antibody;
(2) ouabain-melittin conjugate;
(3) lipid vesicles containing sequestered alkaline phosphatase; and
(4) p-nitrophenyl phosphate
in proportions such that the interaction of unbound ouabain-melittin conjugate and said lipid vesicles results in the conversion of said p-nitrophenyl phosphate by said alkaline phosphatase; and
(B) measuring the concentration of p-nitrophenlate anion produced which is related to the amount of said digoxin initially present in said liquid medium.

36. A conjugate for the detection of an analyte in a test sample, comprising in combination:
(1) cytolysin means for altering the permeability of a membrane of a vesicle, said means being conjugaed to
(2) an antibody molecule capable of binding to the analyte.

37. The conjugate of claim 36 wherein the antibody molecule is a monovalent antibody molecule selected from the group consisting of Fab, Fab', and half-molecules.

38. The conjugate of claim 36 wherein the cytolysin is selected from the group consisting of aerolysin, amphotericin B, alamethicin, A-23187 (calcium ionophore), ATP translocase, cerolysin, diptheria toxin, filipin, gramicidin, melittin, nigericin, nystatin, polymyxin B, *Staphylococcus aureus* toxin α, β, γ, or δ, Streptolysin O, Streptolysin S, tubulin and valinomycin.

39. The conjugate of claim 8 wherein the cytolysin is mellitin.

40. A heterogeneous immunoassay for detecting an analyte in a liquid sample, comprising:
(1) forming a reaction mixture by contacting the sample with a cytolysin/anti-analyte antibody conjugate in immunochemical excess over the analyte, whereby a fraction of said conjugate binds to analyte to form a complex and a fraction of said conjugate remains free,
(2) contacting the reaction mixture with a solid phase having analyte or analyte-analog bound thereto to separate the complex from the free conjugate, and
(3) contacting either the complex or the free conjugate with vesicles having marker material sequestered therein, whereby the permeability of the vesicle increases, thereby releasing marker material,
(4) measuring the amount of released marker material, and
(5) relating the amount of released marker material to the amount of analyte initially present in the test sample.

* * * * *